(12) United States Patent
Martinez

(10) Patent No.: US 12,329,634 B2
(45) Date of Patent: Jun. 17, 2025

(54) OPTICAL TISSUE MEASUREMENT

(71) Applicant: Edwards Lifesciences Corporation, Irvine, CA (US)

(72) Inventor: Carolyn Sue Martinez, Santa Ana, CA (US)

(73) Assignee: EDWARDS LIFESCIENCES CORPORATION, Irvine, CA (US)

(*) Notice: Subject to any disclaimer, the term of this patent is extended or adjusted under 35 U.S.C. 154(b) by 1238 days.

(21) Appl. No.: 17/013,438

(22) Filed: Sep. 4, 2020

(65) Prior Publication Data

US 2020/0397946 A1 Dec. 24, 2020

Related U.S. Application Data

(63) Continuation of application No. PCT/US2019/020827, filed on Mar. 5, 2019.

(60) Provisional application No. 62/638,581, filed on Mar. 5, 2018.

(51) Int. Cl.
| | |
|---|---|
| *A61F 2/24* | (2006.01) |
| *A61L 27/24* | (2006.01) |
| *A61L 27/36* | (2006.01) |
| *A61L 31/00* | (2006.01) |
| *G01N 21/21* | (2006.01) |

(Continued)

(52) U.S. Cl.
CPC ............ *A61F 2/2415* (2013.01); *A61L 27/24* (2013.01); *A61L 27/3625* (2013.01); *A61L 27/3629* (2013.01); *A61L 27/3691* (2013.01); *A61L 31/005* (2013.01); *G05B 19/4097* (2013.01); *A61L 2430/20* (2013.01); *G01N 21/21* (2013.01); *G01N 21/5907* (2013.01); *G05B 2219/36199* (2013.01); *G05B 2219/45172* (2013.01)

(58) Field of Classification Search
CPC ............ A61L 27/3641; A61L 27/3625; A61L 27/3604; A61L 27/3629; A61F 2/2415
See application file for complete search history.

(56) References Cited

U.S. PATENT DOCUMENTS

| | | | |
|---|---|---|---|
| 2004/0024452 A1* | 2/2004 | Kruse | A61F 2/2415 623/2.12 |
| 2008/0147179 A1* | 6/2008 | Cai | A61L 27/3645 623/2.4 |

(Continued)

OTHER PUBLICATIONS

Polarized Light Microscopy (www.microscopyu.com/techniques/polarized-light/polarized-light-microscopy; Aug. 7, 2016).*

(Continued)

*Primary Examiner* — Carolyn A Pehlke
(74) *Attorney, Agent, or Firm* — Calfee, Halter & Griswold LLP

(57) ABSTRACT

An optical method for determining collagen bundle orientation in bovine pericardium includes the use of a system having a light source which transmits light through a first polarizer, a tissue for making a prosthetic valve leaflet, and a second polarizer, where the light then illuminates a detector plate. The light that illuminates the detector plate is used to determine the orientation of collagen fiber bundles. The orientation of the collagen fiber bundles is used to determine where to cut the leaflet edges.

20 Claims, 10 Drawing Sheets

(51) Int. Cl.
  *G01N 21/59* (2006.01)
  *G05B 19/4097* (2006.01)

(56) References Cited

U.S. PATENT DOCUMENTS

2011/0301700 A1* 12/2011 Fish ................ A61F 2/2418
  156/60
2017/0086972 A1* 3/2017 Braido ................ A61F 2/2412

OTHER PUBLICATIONS

Rieppo, Jarno, et al. "Practical considerations in the use of polarized light microscopy in the analysis of the collagen network in articular cartilage." Microscopy research and technique 71.4 (2008): 279-287.*

Polarized Light Microscopy (https://micro.magnet.fsu.edu/primer/techniques/polarized/polmicroalignment.html, Nov. 13, 2015).*

* cited by examiner

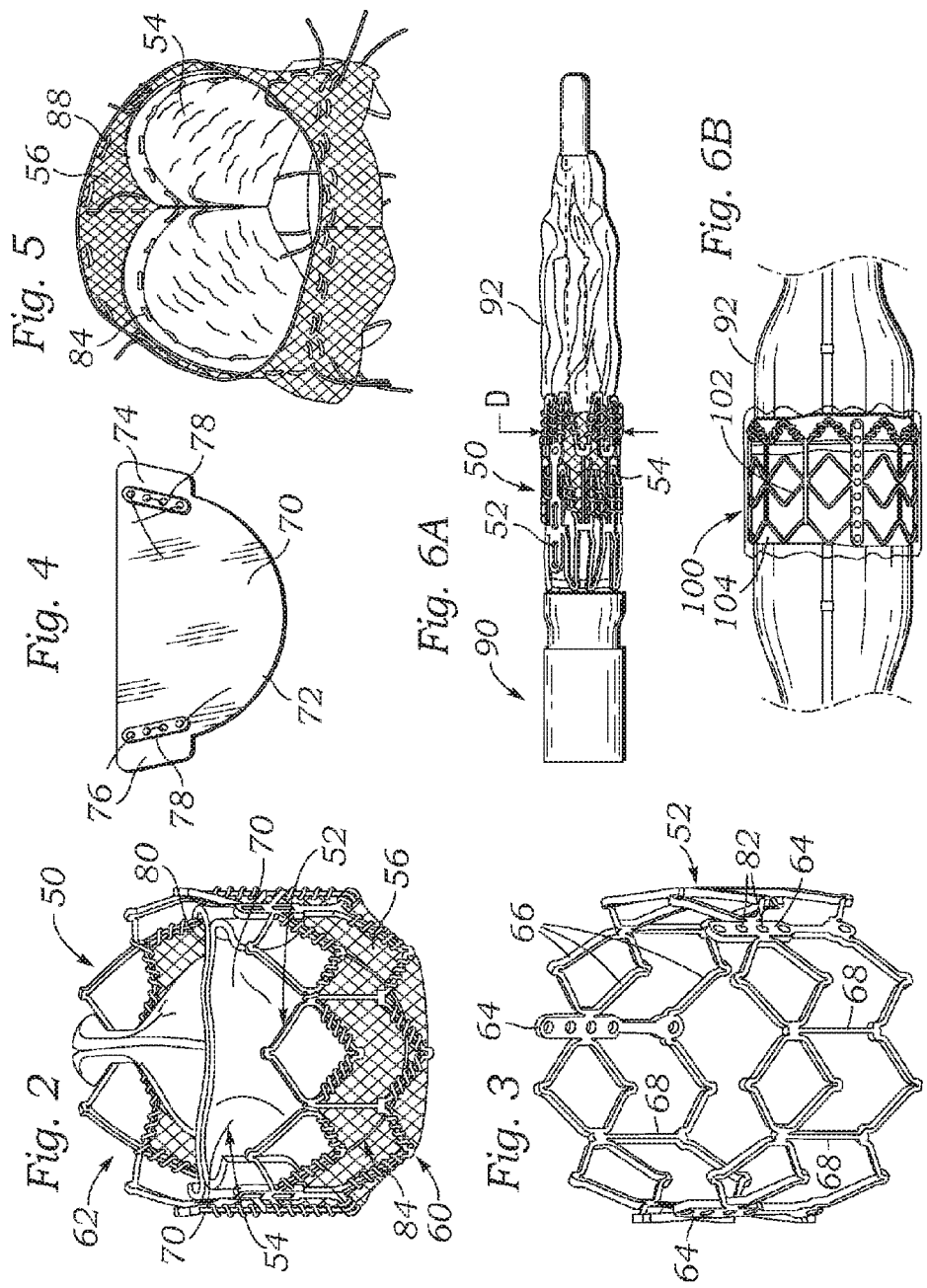

OPTICAL TISSUE MEASUREMENT

This application is a continuation of International Patent Application No. PCT/US2019/020827, filed Mar. 5, 2019, which claims the benefit of U.S. Patent Application No. 62/638,581, filed Mar. 5, 2018, the entire disclosures of which are incorporated by reference herein for all purposes.

The present application relates to the measurement of the orientation and density of collagen fibers of bioprosthetic tissues for use in implants, and more particularly, to an optical measurement of the orientation and density of collagen fibers of bioprosthetic tissue for use in prosthetic heart valves. An optical non-destructive method for determining the orientation and density of collagen bundles in bovine pericardial tissue is provided.

U.S. Pat. No. 9,498,288 (herein "the '288 Patent") discloses methods of conditioning sheet bioprosthetic tissue and is incorporated herein by reference in its entirety. As is explained in the background of the '288 Patent, medical technology has long been capable of replacing damaged or diseased heart valves through open heart surgery. Such valves have included mechanical devices as well as those using biological material from humans (homograft tissue) and animals (xenograft tissue). The two primary types of prosthetic heart valves known in the art are mechanical valves and bioprosthetic valves. Bioprosthetic valves may be formed from an intact, multi-leaflet porcine (pig) heart valve, or by shaping a plurality of individual flexible leaflets out of bovine pericardial tissue or other materials, and combining the leaflets to form the valve.

The pericardium is a sac around the heart of vertebrate animals which contains lubricating fluid, and bovine (cow) pericardium is commonly used to make individual leaflets for prosthetic heart valves. A good discussion of the various physical properties of fixed bovine pericardium is given in Simionescu, et al., "Mapping of Glutaraldehyde-Treated Bovine Pericardium and Tissue Selection for Bio-prosthetic Heart Valves", *Journal of Bio-Medical Materials Research*, Vol. 27, 697-704, John Wiley & Sons, Inc., 1993. Simionescu, et al. recognized the variations in physical properties of the pericardial tissue, even in the same pericardial sac.

The pericardial sac consists of two distinct elements of tissue. The visceral or serous layer is of very thin translucent tissue most adjacent the heart which is not used to construct artificial heart valve leaflets. This inner layer of the pericardium is conical and surrounds the heart and the roots of the great blood vessels. The parietal pericardial membrane is a thicker membrane of multi-layered connective tissue covered with adipose tissue. The outside fat/adipose tissue is removed (e.g., peeled off) when harvested. The remaining multi-layered fibrous tissue primarily contains collagen fibers with a generally fibrous outer surface and a smooth inner surface. This remaining membrane is used for making the leaflets for artificial heart valves.

A number of steps in a typical commercial process for preparing pericardial tissue for heart valve leaflets are illustrated in FIG. 1. First, a fresh pericardial sac 20 is obtained from a regulation slaughterhouse. The sac 20 is then cut open along predetermined anatomical landmarks, as indicated at 22. The sac is then flattened at 24 and typically cleaned of excess fat and other impurities. After trimming obviously unusable areas, a window 26 of tissue is fixed, typically by immersing in an aldehyde to cross-link the tissue, and then quarantined for a period of about two weeks. Normally, two windows of 4 to 6 inches on a side can be obtained from one bovine pericardial sac. Rough edges of the tissue window 26 are removed and the tissue bio-sorted to result in a tissue section 28. The process of bio-sorting involves visually inspecting the window 26 for unusable areas, and trimming the section 28 therefrom. Subsequently, the section 28 is further cleaned as indicated at 30.

The section 28 is then placed flat on a platform 32 for thickness measurement using a contact indicator 34. The thickness is measured by moving the section 28 randomly around the platform 32 while a spindle 36 of the indicator 34 moves up-and-down at various points. The thickness at each point is displayed at 38 and recorded by the operator. The contact indicator measurements are contact and compressive measurements, and spatial resolution of the measurements is directly related to the gage foot size. After sorting the measured sections 28 by thickness, as indicated at 40, leaflets 42 are die cut from the sections, with thinner leaflets 42 generally being used for smaller valves, and thicker leaflets being used for larger valves. Of course, this process is relatively time-consuming and the quality of the final leaflets is dependent at several steps on the skill of the technician. Moreover, the number of leaflets obtained from each sac is inconsistent, and subject to some inefficiency from the manual selection process. One solution to this time-consuming manual process is provided in U.S. Pat. No. 6,378,221 to Ekholm, et al., in which a three-axis programmable controller manipulates a pericardial sheet with respect to a thickness measurement head to topographically map the sheet into similar thickness zones for later use. However, even with advanced methods the variability of the bovine pericardium results in an extremely low yield of sheet usable for heart valve leaflets; averaging fewer than 2 sheets per sac. Typically, harvested bovine pericardial tissue ranges in thickness from 250 microns up to 700 microns, though most of the material is between 300-700 microns thick.

Valves using flexible leaflets, such as those made of bovine pericardial tissue, have acquired increased significance of late because these valves may be implanted by other than open heart surgery. The valves are constructed using radially expandable stents with flexible (e.g., pericardial) leaflets attached. Implant methods include compressing the valve radially by a significant amount to reduce its diameter or delivery profile, inserting the valve into a delivery tool, such as a catheter or cannula, and advancing the delivery tool to the correct anatomical position in the heart. Once properly positioned, the valve is deployed by radial expansion within the native valve annulus, either through self-expanding stent structure or with an expansion balloon. The collapsed valve in the catheter may be introduced through the vasculature, such as through the femoral artery, or more directly through an intercostal incision in the chest. The procedure can be accomplished without open heart surgery and possibly without stopping the heart during the procedure.

One example of percutaneous heart valve delivery is U.S. Pat. No. 6,908,481 to Cribier and Edwards Lifesciences of Irvine, Calif., which shows a valve prosthesis with an expandable frame on which a collapsible valvular structure is mounted. Another compressible/expandable heart valve is shown in U.S. Patent Publication No. 2010/0036484, also from Edwards Lifesciences. Further examples of such methods and devices are disclosed in U.S. Pat. No. 7,621,948 and US Patent Publication No. 2006/0259136. The disclosures of each of these references are incorporated herein by reference.

Optical measurement methods for tissue thickness can fit into one or more of the general categories of interferometry (OCT), ultrasonic imaging, or involving the reflected light and analysis of a precise Z-stack typically associated with advanced microscopy. These methods are typically used for small sample sizes.

SUMMARY

An optical method for determining collagen bundle orientation in bovine pericardium includes the use of a system having a light source which transmits light through a first linear polarizer, a tissue for making a prosthetic valve leaflet, and a second linear polarizer, where the light then illuminates a detector plate. The light that illuminates the detector plate is used to determine the orientation of collagen fiber bundles. The orientation of the collagen fiber bundles is used to determine where to cut the leaflet edges.

An example provides a method for manufacturing a bioprosthetic tissue leaflet from a collagenous tissue, the method comprising: illuminating a piece of tissue comprising collagen with a light source having a linear polarization; passing light transmitted through the piece of tissue through a linear polarizer; detecting a pattern in the light passed through the linear polarizer; determining an orientation or a density of collagen bundles in at least a portion of the piece of tissue from the detected pattern; selecting an area on the piece of tissue for a bioprosthetic tissue leaflet based on the orientation or density of collagen bundles; and cutting the bioprosthetic tissue leaflet including the selected area.

Illuminating the piece of tissue can include illuminating a piece of pericardium, dura mater, peritoneum, diaphragm, or intestinal submucosa. Illuminating the piece of tissue can comprise illuminating a piece of pericardium. Illuminating the piece of pericardium can comprise illuminating a piece of bovine or porcine pericardium. Illuminating the piece of tissue can include illuminating a piece of wet tissue. Illuminating the piece of tissue can include illuminating a piece of dry tissue. Illuminating the piece of tissue can include illuminating a piece of fixed tissue. The method of any of claims 1-6, wherein illuminating the piece of tissue comprises illuminating a piece of unfixed tissue. Illuminating the piece of tissue can include changing an angle of incidence between the light source and the piece of tissue. Illuminating the piece of tissue can include illuminating the piece of tissue with a specific wavelength of light.

Passing light transmitted through the piece of tissue through the linear polarizer can include passing light transmitted through the piece of tissue through a linear polarizer parallel with the linear polarization of the light source. Passing light transmitted through the piece of tissue through the linear polarizer can include passing light transmitted through the piece of tissue through a linear polarizer perpendicular to the linear polarization of the light source. Passing light transmitted through the piece of tissue through the linear polarizer can include passing light transmitted through the piece of tissue through a linear polarizer that is not parallel with nor perpendicular to the linear polarization of the light source.

Detecting the pattern can include projecting a pattern on a detector plate. Detecting the pattern can include displaying a pattern on a monitor. Detecting the pattern can include imaging a pattern with a camera. Detecting the pattern can include storing a pattern on a computer. Detecting the pattern can include detecting a pattern including at least one elongate feature, line, streak, or band.

Determining the orientation or the density can include determining an intensity of at least a portion of the pattern. Determining the orientation or the density can include determining a direction of at least a portion of the pattern. Determining the orientation or the density can include determining an orientation.

Selecting the area can include selecting an area in which the collagen bundle orientations are randomly distributed. Selecting the area can include selecting an area in which the collagen bundle orientations are aligned. Selecting the area can include laying-out a free-edge of the bioprosthetic tissue leaflet parallel with the alignment of the collagen bundles.

Cutting the bioprosthetic tissue leaflet can include die cutting a bioprosthetic tissue leaflet. Cutting the bioprosthetic tissue leaflet can include laser cutting a bioprosthetic tissue leaflet.

The method can include relatively rotating the polarizations of the linear polarization of the light source and of the linear polarizer.

Another example provides a method for manufacturing a bioprosthetic heart valve, the method comprising: securing to a stent a plurality of bioprosthetic leaflets manufactured as disclosed herein, wherein the plurality of bioprosthetic leaflets is arranged as a one-way valve permitting forward blood flow from a first end to a second end of the bioprosthetic heart valve, and blocking reverse blood flow from the second end to the first end of the bioprosthetic heart valve.

The bioprosthetic heart valve can be a surgically implantable bioprosthetic heart valve. The bioprosthetic heart valve can be a transcatheter bioprosthetic heart valve, and wherein the stent is radially collapsible and expandable. The bioprosthetic heart valve can be a bioprosthetic aortic valve. The bioprosthetic heart valve can be a bioprosthetic mitral valve. The bioprosthetic heart valve can be a bicuspid valve or a tricuspid valve.

Another example provides a bioprosthetic tissue leaflet comprising a free edge and a cusp edge, the bioprosthetic tissue comprising a collagenous tissue, wherein an alignment of the collagen bundles in the bioprosthetic tissue is parallel with the free edge.

Another example provides a bioprosthetic tissue valve comprising a stent and a plurality of the bioprosthetic tissue leaflets, each comprising a free edge and a cusp edge, the bioprosthetic tissue comprising a collagenous tissue, wherein an alignment of the collagen bundles in the bioprosthetic tissue is parallel with the free edge, the plurality of bioprosthetic leaflets is arranged as a one-way valve permitting forward blood flow from a first end to a second end of the bioprosthetic heart valve, and blocking reverse blood flow from the second end to the first end of the bioprosthetic heart valve.

Another example provides a system for measuring collagen properties of tissue that can include: a light source; a first polarizer; a second polarizer; a mounting platform; tissue for making a prosthetic valve leaflet mounted in the mounting platform; and a detector plate; wherein the light source is positioned at a first end of the system, directed towards the detector plate, the detector plate is positioned at a second end of the system, the first polarizer is adjacent the light source, the second polarizer is adjacent the detector plate, and the mounting platform and the tissue is between the first polarizer and the second polarizer.

The first polarizer can transmit linearly polarized light in a first orientation, and the second polarizer can be oriented to extinguish the linearly polarized light in the first orientation. The second orientation can be rotatable between a first position that polarizes the light waves in a same direction as the first polarizer and a second position that polarizes the light waves in an orthogonal direction to the first polarizer.

The system can include a computer processor and a monitor electronically connected to the detector plate.

The linearly polarized light waves can be transmitted through the tissue for making a prosthetic valve leaflet, and the linearly polarized light waves may be rotated as they pass through collagen bundles in the tissue for making a prosthetic valve leaflet.

The rotated light waves may be polarized in the second orientation as they pass through the second polarizer, and the light waves linearly polarized by the first polarizer that are not rotated by the collagen bundles may be extinguished by the second polarizer. The rotated light waves may become elliptically polarized and partially pass through the second polarizer, and the light waves that are not rotated by the collagen bundles may be extinguished by the second polarizer. The light waves passing through the second polarizer can illuminate the detector plate.

The tissue for making a prosthetic valve leaflet can include tissue from a bovine pericardium. The tissue for making a prosthetic valve leaflet can be treated with one or more of ethanol or glutaraldehyde.

Another example provides a method of measuring the collagen properties of tissue that can include the steps of: positioning a tissue for making a prosthetic valve leaflet comprising collagen bundles on a mounting platform in between a first polarizer and a second polarizer; transmitting light waves from a light source, through the first polarizer to create linearly polarized light waves having a first orientation; transmitting the linearly polarized light waves through the tissue for making a prosthetic valve leaflet, wherein some of the linearly polarized light waves are rotated to become rotated light waves as they pass through collagen bundles in the tissue for making a prosthetic valve leaflet; transmitting the rotated light waves from the tissue for making a prosthetic valve leaflet to the second polarizer so that the polarized light is extinguished and the rotated light is polarized as it passes through the second polarizer; illuminating the detector plate with the linearly polarized light from the second polarizer; and viewing the linearly polarized light waves illuminating the detector plate to determine the orientation and density of the collagen bundles in the tissue for making a prosthetic valve leaflet.

The orientation of the light waves illuminating the detector plate can correspond to the orientation of the collagen bundles. The brightness of the light waves received by the detector plate can corresponds to the density of the collagen bundles. The method can include the step of outputting a visual representation of the light waves on the detector plate to a monitor.

Another example provides a method of making leaflets for a valve implant that can include the steps of: determining collagen bundle orientation of a tissue for making a prosthetic valve leaflet by: transmitting light waves from a light source through a first polarizer to create linearly polarized light waves in a first orientation, transmitting the linearly polarized light waves through the tissue for making a prosthetic valve leaflet, wherein the linearly polarized light waves are rotated as they pass through collagen bundles in the tissue for making a prosthetic valve leaflet, transmitting the rotated light waves through a second polarizer wherein the rotated light is linearly polarized in a second orientation as it passes through the second polarizer, illuminating the detector plate with the linearly polarized light from the second polarizer; and viewing an orientation of the polarized light waves on the detector plate, wherein a spatial distribution of transmitted light corresponds to the orientation of the collagen bundles in the tissue for making a prosthetic valve leaflet; using the orientation of the polarized light waves to determine where to cut at least one leaflet from the tissue for making a prosthetic valve leaflet.

The method can include the step of determining a length along which the collagen bundles extend and cutting an upper edge on the at least one leaflet along the length. The method can include the step of cutting a lower edge, and two commissure flaps extending between the lower edge and the upper free edge. The method can include the step of rotating the second polarizer until a first set of polarized light waves appear on the detector plate. The method can include the step of adjusting a contrast on the detector plate to determine the density of the collagen bundles in the tissue for making a prosthetic valve leaflet. The method can include the step of rotating the second polarizer until a second set of polarized light waves appears on the detector plate.

BRIEF DESCRIPTION OF THE DRAWINGS

Further features and advantages of the invention will become apparent from the description of embodiments using the accompanying drawings. In the drawings:

FIG. 2 is a perspective view of a representative embodiment of a prosthetic heart valve that may be made with conditioned tissue;

FIG. 3 is a perspective view of a support frame that can be used in the prosthetic valve of FIG. 2;

FIG. 4 is a flattened view of a leaflet of the valve shown in FIG. 2;

FIG. 5 is a bottom perspective view of a valve leaflet structure connected to a reinforcing skirt to form a leaflet assembly;

FIG. 6A depicts a side view of an exemplary prosthetic heart valve crimped on a balloon delivery catheter;

FIG. 6B shows the prosthetic valve of FIG. 6A mounted on the balloon delivery catheter and in its expanded state;

DETAILED DESCRIPTION

Figure 1:
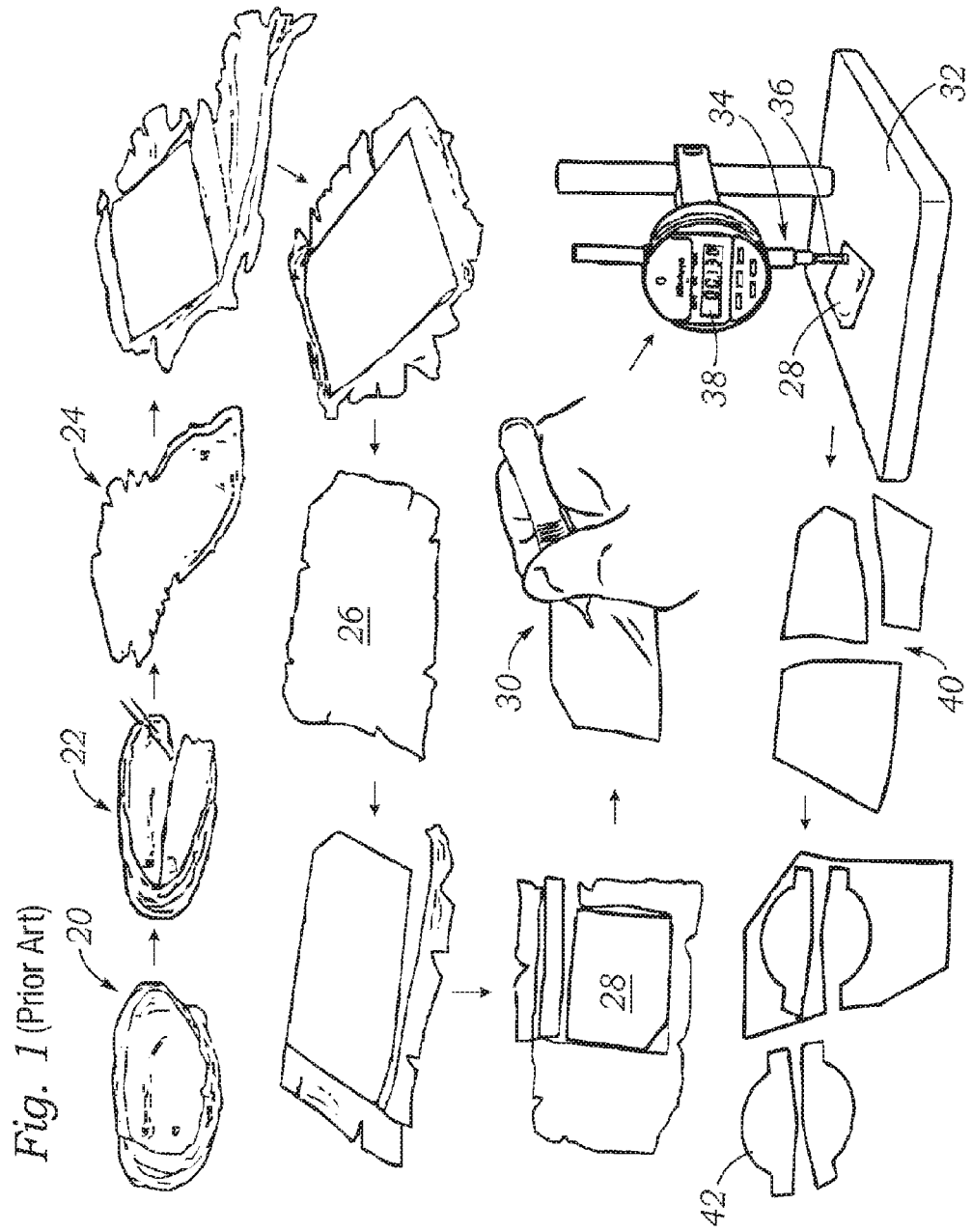
FIG. 1 illustrates a sequence of prior art steps for preparing and measuring the thickness of bovine pericardial tissue prior to forming leaflets from the tissue.

Disclosed herein are various embodiments of an apparatus and method of use, which rely on optical properties and polarized light transmittance of a tissue to measure collagen bundle density and/or collagen bundle orientation in a bioprosthetic tissue such as a bovine or porcine pericardium. The collagen bundle orientation and/or collagen bundle density is then used to optimize the fabrication of prosthetic valve leaflets. Collagen bundles are made of collagen fibers. The collagen bundle density can be the density of the collagen fibers in a bundle and/or the density of the collagen bundles of an area of the tissue. Exemplary embodiments of methods of visually and quantitatively measuring the collagen bundle orientation and collagen bundle density of a tissue sample, as well as the use of these measurements to optimize the fabrication of heart valve leaflets are provided herein. In particular, the system and method described herein measures the light transmittance of wet bovine pericardial tissue to quickly determine its collagen bundle orientation and/or collagen bundle density. The system and method described herein is used to determine collagen bundle orientation in bovine pericardial tissue supplied for use in making heart valves. For example, the non-contact measurement apparatus and method can be used to measure the collagen bundle orientation and/or collagen bundle density of any of the tissues described in the background and/or the '288 patent. In addition, the apparatus and method disclosed herein can be used with any of the methods and apparatuses disclosed by the '288 patent, to provide an additional step of determining the collagen bundle orientation and/or collagen bundle density so the tissue can be cut to maximize its strength and elastic properties in the heart valve leaflet application.

The apparatus and method for optically determining collagen bundle orientation is not limited to the measurement of bovine pericardial tissue. The apparatus and method can be used to measure the collagen bundle orientation of any tissue through which light can be transmitted. For example, the methods and apparatuses are not limited to heart valves and can be used for any tissue to make any implant or other device.

By optimizing the collagen bundle orientation and/or collagen bundle density, the valve leaflets can be made thinner without sacrificing any strength or durability. The thinner prosthetic valve leaflets enable crimping of the valve down to a size that can pass through the delivery tool.

The collagen bundle orientation and/or collagen fiber density can be used to optimize the valve leaflets disclosed by the '288 Patent. The leaflets are desirably incorporated in expandable prosthetic heart valves that are initially crimped (or even rolled) into a small delivery profile or diameter to be passed through a catheter or other delivery system and then expanded at the implantation site, typically a valve annulus. The heart valves comprise structural stent bodies with a plurality of flexible leaflets incorporated therein. Various materials are suitable for the stent body, although certain nickel-titanium alloys (e.g., nitinol) are preferred for their super-elasticity and biocompatibility.

Forming prosthetic heart valve leaflets to be thinner helps reduce the delivery size of expandable valves. Optimizing the leaflets based on the collagen bundle orientation and/or the collagen bundle density to forming thinner leaflets is also advantageous for conventional heart valves.

The orientations and/or densities of the collagen fibers of various tissues may be optimized before being cut and used for the leaflets. One preferred tissue for use in the primary application of heart valve leaflets is bovine parietal pericardial membrane. Though the thickness and strength of bovine pericardial tissue is considered desirable for longer lasting valves, other bioprosthetic tissue such as porcine, equine, bison, kangaroo, and other mammalian pericardium, including human, may be used. Furthermore, tissue from other anatomical sources may be used, such as dura mater, peritoneum, diaphragm, intestinal submucosa, or others. Any tissue membrane that has a suitable durability and elasticity is a candidate, though those of skill in the art will appreciate that certain materials may be better suited for any one specific application. In general, tissues that contain fibrous collagen, in particular, classed as Type I or Type III collagen, and elastic fibers or elastin may be suitable for use in fabricating heart valve leaflets. Other potential types of collagen that can be used are hybrid natural collagen solution or electrospun collagen elastin fabric. Also, certain so-called engineered tissue may be used, which are synthesized by growing collagenous tissue over a typically mesh frame or scaffold. These are collectively referred to as "tissue membranes." Although the discussion herein focusses on pericardial tissue and the manufacture of leaflets for heart valves, the devices, methods, and systems are equally applicable to these other materials, as well as for all other devices and applications using these materials.

As mentioned above, the pericardial sac consists of two or more distinct layers, one side being relatively smooth while the opposite surface comprises connective tissue covered with adipose tissue, some of which is peeled off when harvested, and is thus fibrous. In some cases, the thickness of the fibrous adipose tissue side may also be reduced to produce a uniformly thin membrane, preferably below 300 microns for use in collapsible/expandable valves.

With reference to FIG. 2, a heart valve 50 is shown. A commercially available valve implant of the type illustrated by FIG. 2 that has leaflets made of bovine pericardial tissue is the Edwards SAPIEN 3 transcatheter heart valve. The tissue for other valves and prosthetics that use tissue samples can also be measured with the system and method as the exemplary embodiment described herein.

In an exemplary embodiment, the orientations and/or densities of the collagen fibers of the valve tissues are optimized before being cut and used for the leaflets of the valve. The valve 50 will be described in some detail, but more specifics on the valve structure may be found in U.S. Patent Publication No. 2010/0036484, filed Jun. 8, 2009, entitled "LOW PROFILE TRANSCATHETER HEART VALVE," and assigned to Edwards Lifesciences, the disclosure of which is incorporated herein by reference. Alternatively, another minimally-invasive valve that may utilize valve leaflets that are optimized based on collagen fiber orientations and/or densities is found in U.S. Pat. No. 6,733,525, issued May 11, 2004, entitled "ROLLED MINIMALLY INVASIVE HEART VALVES AND METHODS OF USE," which disclosure is expressly incorporated herein by reference.

Valve leaflets 54 that are cut to optimize strength and durability based on collagen fiber orientation and/or collagen fiber density can be used in a wide variety of different heart valves. The heart valves can be of the type that implanted during an open-heart surgery or can be of the type that are implanted via a catheter, and can be prostheses for any of the four native valves: aortic, mitral, pulmonic or tricuspid. An example of one of the many different types of heart valves that can use valve leaflets that are cut to optimize strength and durability based on collagen fiber orientation and/or collagen fiber density is illustrated by FIGS. 2-5. In this example, the valve 50 comprises a structural frame, or stent 52, a flexible leaflet structure 54 supported by the frame, and an optional flexible skirt 56 secured to the outer surface of the leaflet structure. The illustrated valve 50 may be implanted in the annulus of the native aortic valve, but also can be adapted to be implanted in other native valves of the heart or in various other ducts or orifices of the body. Valve 50 has a "lower" or inflow end 60 and an "upper" or outflow end 62. Blood flows upward freely through the valve 50, but the flexible leaflet structure 54 closes to prevent reverse downward flow. The flexible leaflet structure 54 thus provides flexible fluid occluding surfaces to enable one-way blood flow.

Valve 50 and frame 52 are configured to be radially collapsible to a collapsed or crimped state for introduction into the body on a delivery catheter and radially expandable to an expanded state for implanting the valve at a desired location in the body (e.g., the native aortic valve). Frame 52 can be made of a plastically-expandable material that permits crimping of the valve to a smaller profile for delivery and expansion of the valve using an expansion device such as the balloon of a balloon catheter. Exemplary plastically-expandable materials include, without limitation, stainless steel, a nickel based alloy (e.g., a nickel-cobalt-chromium alloy), polymers, or combinations thereof. Alternatively, valve 50 can be a so-called self-expanding valve wherein the frame is made of a self-expanding or shape-memory material such as nitinol. A self-expanding valve can be crimped and held in the collapsed state with a restraining device such as a sheath covering the valve. When the valve is positioned at or near the target site, the restraining device is removed to allow the valve to self-expand to its expanded, functional size.

Referring also to FIG. 3 (which shows the frame alone for purposes of illustration), the frame 52 is a generally tubular, stent-like structure having a plurality of angularly spaced, vertically extending struts, or commissure attachment posts 64. The posts 64 in FIG. 3 are somewhat modified from those shown in FIG. 2. The posts 64 are interconnected via several rows of circumferentially extending struts 66. Thinner vertical (axial) struts 68 intermediate the commissure attachment posts 64 connect to and extend between adjacent horizontal rows of struts 66.

In the example, leaflet structure 54 comprises three separate connected leaflets 70 such as shown in FIG. 4, which can be arranged to collapse in a tricuspid arrangement, as best shown in FIGS. 2 and 5. Each leaflet 70 has a curved lower cusp edge 72 opposite a generally straight upper free edge 74, and two commissure flaps 76 extending between the free edge 74 and the lower edge 72. The curved cusp edge 72 forms a single scallop in the leaflet structure 54. When secured to two other leaflets 70 to form the leaflet structure 54, the curved cusp edges 72 of the leaflets collectively form a scallop-shaped lower edge of the leaflet structure (as best shown in FIG. 5). As further shown in FIG. 4, two optional reinforcing bars 78 can be secured to each leaflet 70 adjacent to flaps 76 (e.g., using sutures). The flaps can then be folded over bars 78 and secured in the folded position using sutures. If desired, each bar 78 can be placed in an optional protective sleeve (e.g., a PET sleeve) before being secured to a leaflet.

Leaflets 70 attach to one another at their adjacent sides to form commissures 80 of the leaflet structure (see FIG. 2 at the edges where the leaflets come together). Leaflet structure 54 can be secured to frame 52 using various techniques and mechanisms. For example, as best shown in FIG. 2, commissures 80 of the leaflet structure desirably are aligned with the support posts 64 and secured thereto using sutures through holes 82 (FIG. 3). The point of attachment of the leaflets to the posts 64 can be reinforced with the optional bars 78 (FIG. 4), which desirably are made of a relatively rigid material (compared to the leaflets), such as stainless steel.

As mentioned, the lower edge of leaflet structure 54 desirably has an undulating, curved scalloped shape. A suture line 84 visible on the exterior of the skirt 56 in FIG. 2 can track the scalloped shape of the leaflet structure 54.

Referring again to FIGS. 2 and 5, the optional skirt 56 can be formed, for example, of polyethylene terephthalate (PET) ribbon. The leaflet structure 54 attaches to the skirt via a thin PET reinforcing strip 88 (or sleeve), FIG. 5, which enables a secure suturing and protects the pericardial tissue of the leaflet structure from tears. The leaflet structure 54 is sandwiched between skirt 56 and the reinforcing strip 88. The suture 84, which secures the reinforcing strip and the leaflet structure 54 to skirt 56 can be any suitable suture, and desirably tracks the curvature of the bottom edge of leaflet structure 54, as seen on the exterior of the skirt 56 in FIG. 2. The skirt 56 and leaflet structure 54 assembly resides inside of frame 52 and secures to the horizontal struts 66 via a series of zigzag pattern sutures 86, as shown in FIG. 2.

To assemble, the heart valve leaflets 70 are cut from a membrane such as bovine pericardium based on collagen bundle orientations and/or collagen bundle densities and thinned, conditioned or otherwise shaped in accordance with the principles described herein. In the expandable valve 50 described above, the leaflets 70 attach within the tubular stent frame 52 and the three adjacent pairs of free edges 74 meet in the middle of the valve at coapting lines oriented equiangularly with respect to one another. The free edges 74 billow inward to meet along the coapting lines.

FIG. 6A shows the prosthetic heart valve 50 crimped onto balloon 92 of a balloon delivery catheter 90. As explained herein, the thinning of the bioprosthetic tissue applied to the material for the leaflets helps enable the outer diameter D of the assembled valve and balloon catheter to be as small as about 6 mm or smaller. Expanded prosthetic heart valve sizes are typically anywhere between about 20 mm up to about 30 mm.

FIG. 6B shows an alternative embodiment of a prosthetic aortic valve 100 comprising a frame 102 and a leaflet structure 104 mounted to the inside of the frame (e.g., using sutures as shown and described above). The valve 100 is shown in its expanded state after the expansion balloon 92 has been inflated. The size of the expanded valve 100 varies depending on the patient, typically between about 22 and about 40 mm.

Implant methods include compressing the valve 50 radially by a significant amount to reduce its diameter or delivery profile, inserting the valve into a delivery tool, such as a catheter or cannula, and advancing the delivery tool to the correct anatomical position in the heart. Once properly positioned, the valve 50 is deployed by radial expansion within the native valve annulus with the expansion balloon 92. The collapsed valve 50 in the catheter may be introduced through the vasculature, such as through the femoral artery, or more directly through an intercostal incision in the chest. It is desirable for the valve to have a small diameter or profile to facilitate delivery, for example, through the femoral artery. One method for manufacturing smaller crimped or constricted heart valves is to use thinner tissue to make the leaflets 70. The conditioning disclosed in the '288 Patent can reduce the tissue thickness and may also involve smoothing the tissue to result in a thin, constant-thickness membrane from which to cut leaflets. Or, the leaflets may be formed first and then thinned. There are a number of ways to thin the tissue including using laser ablation.

Thinned pericardial membrane may be used in various types of heart valves, including conventional surgical valves. One specific example, of conventional heart valves that may utilize pericardial tissue is the Carpentier-Edwards® PERIMOUNT® line of pericardial bioprostheses, available from Edwards Lifesciences. The basic construction of the PERIMOUNT® valve is seen in U.S. Pat. No. 5,928,281, which disclosure is expressly incorporated herein by reference.

Desirably, pericardial layers used for transcatheter heart valve leaflets have thicknesses of about 250-500 microns, for example, about 250 microns. Only a small percentage of the harvested bovine pericardium falls close to 250 microns thick. Most harvested bovine pericardium is thicker, for example, about 300-700 microns.

The strength of leaflets cut from bovine pericardial tissue varies depending on the collagen bundle and/or fiber orientation. The tissue is strongest along the axis of the collagen bundles/fibers. In practice, the collagen bundles in a piece of bovine pericardium that is large enough to manufacture a leaflet will have multiple orientations. As such, examples using bovine pericardium are directed to determining an average orientation or alignment of the collagen bundles in the leaflet for such materials, and selecting areas or regions with higher average orientations or alignments for manufacturing leaflets. Other types of tissue can have intrinsically greater or less ordered collagen bundle orientations than bovine pericardium. The disclosed methods and apparatuses are used to determine the density and orientation of collagen bundles for any collagenous material. This collagen fiber bundle analysis can be used to reduce the number of processing steps required to make the valve leaflets and results in more uniform collagen bundle/fiber distribution once the leaflets are cut.

Figure 7:
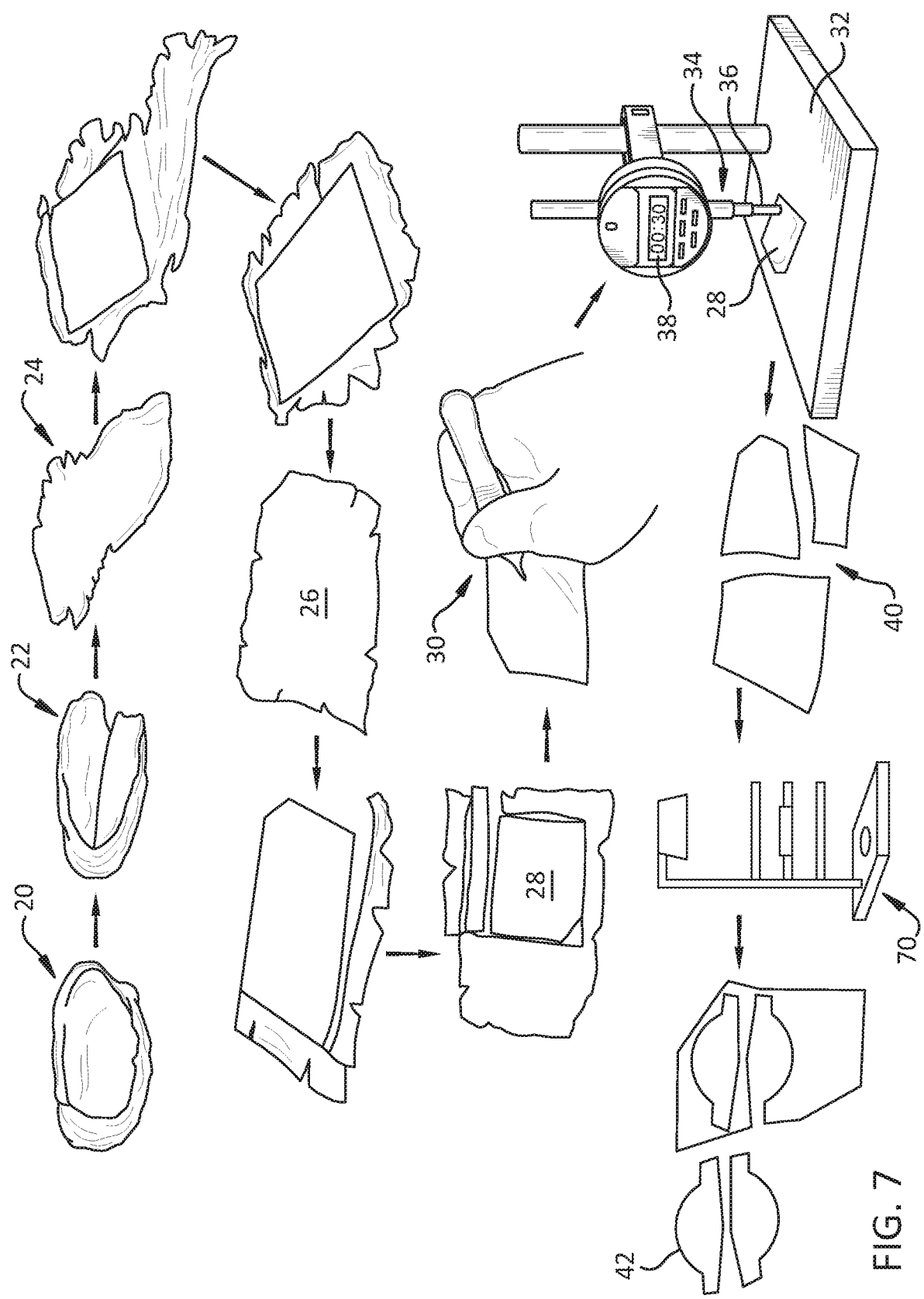
FIG. 7 illustrates a sequence of steps for determining the collagen fiber orientation and density, and preparing and measuring the thickness of bovine pericardial tissue prior to forming leaflets from the tissue.

The methods for determining the collagen bundle orientation and/or density of the collagen bundles of the exemplary embodiments described herein can be incorporated into the method of making implants as described with respect to FIG. 1, and according to U.S. Provisional Application No. 62/638,581, filed Mar. 5, 2018, are incorporated herein by reference. The collagen bundle properties can be measured at various stages throughout the process of forming a leaflet from pericardial tissue. In an exemplary embodiment, the collagen bundle orientation can be determined as a part of the biosorting process, either before or after measuring the thickness of a tissue sample. The collagen bundle properties can also be determined before biosorting, such as after fixing (e.g., cross-linking) the tissue, or after the rough edges of the tissue are removed. The collagen bundle properties can be measured more than once throughout the process, such as before and after thinning the tissue. The collagen properties can be determined before the leaflets are cut, as the properties are useful when deciding the location and orientation in which to cut the leaflets from the tissue sample. FIG. 7 illustrates one exemplary embodiment of using an optical technique to measure the collagen bundle orientation and density, during the method of making an implant with leaflets. In FIG. 7, the density and orientation of the collagen bundles are determined at step 70 with an exemplary embodiment of the system 800 described herein, after the thickness has been measured and the tissue samples have been sorted according to thickness as shown in step 40, and before the die-cutting of the leaflets, as shown in step 42.

The tissue 28 can be wet or dry tissue. The tissue can be pericardial tissue, for example, bovine or porcine pericardial tissue, but can be any suitable collagenous tissue, for example, as set forth above. For example, the tissue can be wet bovine pericardial tissue. Tissue is classified as "wet" when it has been treated with liquid, for example, an aqueous solution, ethanol, or a glutaraldehyde solution, or any other liquid known to be used in the preparation of bioprosthetic tissue and/or tissue samples. For example, the tissue can suitable for dry packaging, for example, glycerolized tissue. The treatment with these fluids can, for example, enhance the accuracy of the measurement, facilitate handling, and/or make the tissue more suitable for use in a prosthetic device. For example, tissue can be treated as described by the '288 Patent. The tissue can be fixed or unfixed. The tissue 28 can be a valve leaflet, an entire pericardial tissue sac, or one or more portions or windows cut from the pericardial sac. Dimensions for a portion or portions to be cut from a pericardial sac can be determined based on the collagen bundle and/or fiber orientation and density derived from the system 800 disclosed herein to provide a higher yield of useable tissue from the pericardial sac than would be otherwise attainable without the system. The system and method to determine the collagen properties herein reduces the number of processing steps and results in more uniform collagen bundle/fiber distribution in the final tissue component, for example, a cut leaflet.

Figure 8:
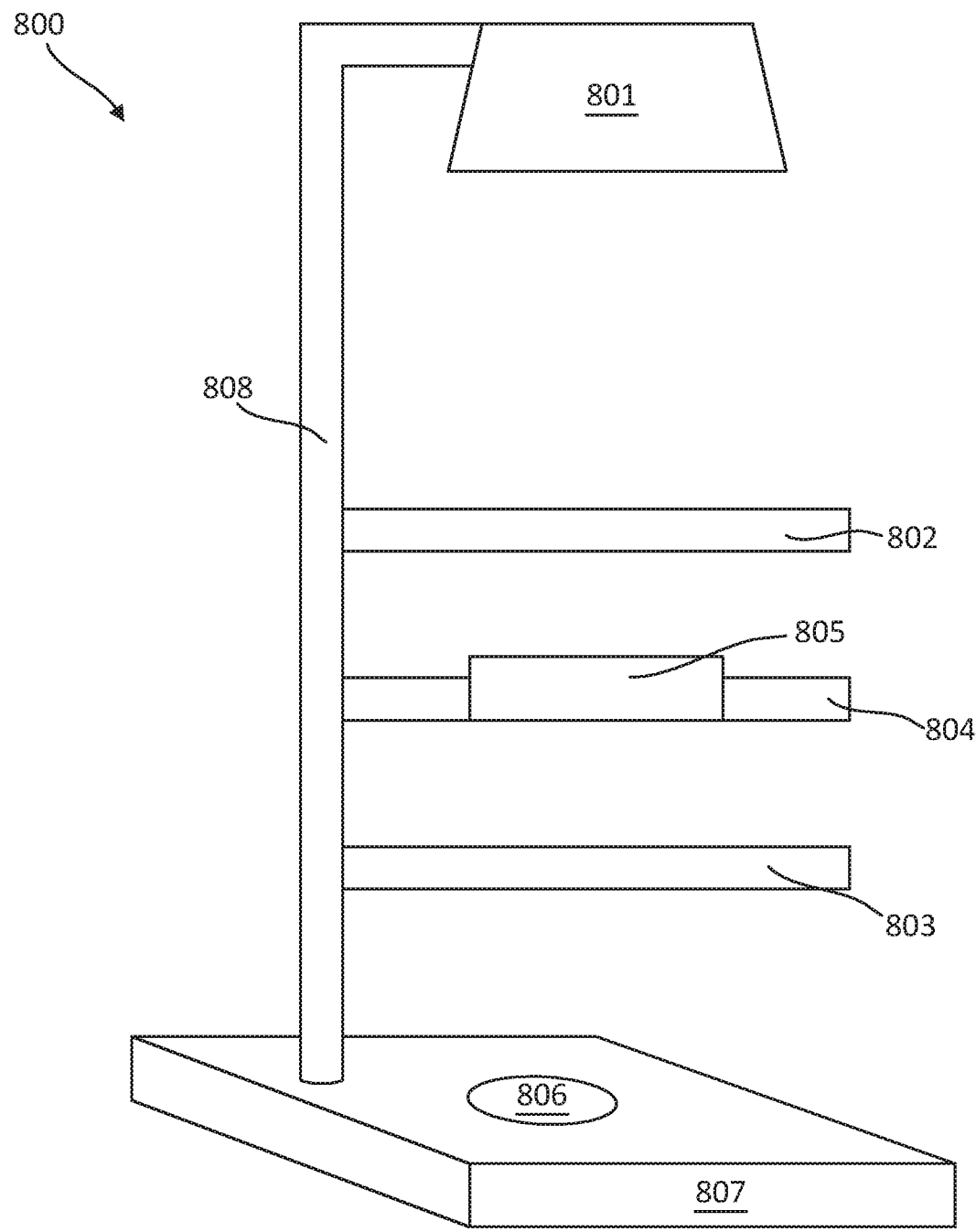
FIG. 8 illustrates an assembly for determining the properties of collagen fiber within a tissue sample according to an exemplary embodiment.

A system using a polarization analysis for determining information about a collagen bundle and/or fiber orientation and/or collagen bundle density of a tissue sample is provided herein. FIG. 8 illustrates such a system 800. The system 800 according to an exemplary embodiment can have a light source 801, a first linear polarizer 802, a second linear polarizer 803, a mounting platform 804 which can have a tissue sample 805 mounted on it, and a detector plate 806. The components can be assembled together with a base 807 and a shaft 808 extending vertically upward from the base. The remaining components are assembled in order: the light source 801, the first polarizer 802, the mounting platform 804 positioned between the first polarizer plate and the second polarizer plate, and the detector plate 806 at the bottom, which can be positioned on the base 807. While the components are ordered with the light source 801 at the top and the detector plate 806 at the bottom of the assembled system in FIG. 8, the system is not limited to such a configuration. In an exemplary embodiment, the light source can be at the bottom of an assembled system, and the detector plate can be at the top. In another exemplary embodiment, the system can be assembled with the components arranged side-by-side, so that the light source is at a first, for example, left, side and the detector plate is a second, for example, right, side. In an example, the components can be arranged side-by-side along a base 807. The components can be in any orientation as long as the light can is directed towards a first polarizer, a tissue sample on the mounting platform, a second polarizer, and the detector plate. The light source can be any light source, and can be an unpolarized white light source. For example, the light source can be a fluorescent light, an incandescent light, or an LED. Some examples use a single wavelength or a plurality of discrete wavelengths of light rather than a white or broadband light source. Some examples include one or more laser light sources. Near IR (NIR) or UV light can also be used, either alone, or in combination with other sources.

The polarizers are optical filters that let light waves of a selected polarization pass through while blocking light waves of other polarizations. The polarizers convert the light from the light source, which illuminates the tissue sample, into polarized light. The description provides examples in which the polarizers are linear polarizers that produce linearly polarized light. The methods and systems can also use circular polarizers or elliptical polarizers (e.g., waveplates), or any combination of linear, circular, and elliptically polarized light and filters, and the description expressly includes these options. The birefringent properties of the collagen bundles/fibers can also be observed without using polarized incident light; that is, without using the first polarizer 802. In most cases, using polarized incident light improves visualization, however, for example, improving contrast.

The mounting platform 804 can be a platform that includes an opening and/or a frame suitable for holding a tissue sample. A tissue sample is placed or held on the mounting platform and remains there while the polarized light passes through it, for determining the collagen bundle properties. The mounting platform can have one or more means or devices for holding the tissue sample in place, for example, clips, clamps, pins, vacuum ports, or the like. The mounting platform can have an indentation around the perimeter of the interior opening in which the tissue sample can sit within while covering the opening. The opening 805 can include a transparent material (e.g., window), a hole, an aperture, or a cutout. The tissue sample can be positioned on the mounting platform so that it is between the polarizers 802, 803. The mounting platform can be arranged for rotation relative to the main or optical axis of the device, which can provide similar results as and can be done in addition to or in place of rotating one or both polarizers, which is discussed below. Some examples of the mounting platform can rotate or tilt on at least one axis perpendicular to the main or optical axis, which be used to adjust an angle of incidence of the light source on the sample, which can improve the visualization or imaging of collagen bundles/fibers with certain orientations in the sample. In some example, the mounting platform is also translatable along one or more axes, which can be helpful, for example, in determining if a particular feature is an optical artifact or not.

The detector plate 806 can be placed at an end of the system opposite the end having the light source. The detector plate receives the light transmitted through the second polarizer. For example, as illustrated in FIG. 8, the detector plate can be placed on or within the base 807 of the apparatus. The detector plate 806 can be a camera or other device for capturing spatial orientation and signal intensity. The detector plate can be coupled to an external monitor and/or a computer with a processor, for displaying the output to a user. A user can also directly visually observe the light or image on the detector plate. The image can also be magnified. A pattern on the detector plate provides information on the collagen properties of the tissue sample. For example, collagen bundles/fibers can generate elongate features following the direction of the bundles. Depending on the density of the aligned bundles, the features appear as line, bands, streaks, or the like. The intensity of the feature can be related to the density of the aligned bundles. Regions in which the bundles are not aligned, for example, random, are associated with crisscrossing features or a diffuse appearance, and generally, lower intensity. As discussed below, the features can be light or dark. The detector plate can be a flat surface which can be illuminated with light, such that illuminated regions and dark regions can be distinguished. The contrast of the light on the detector plate against the unilluminated regions of the detector plate can be adjusted to improve the visualization of the characteristics, (e.g., densities, orientations) of the collagen bundles.

Figure 9A:
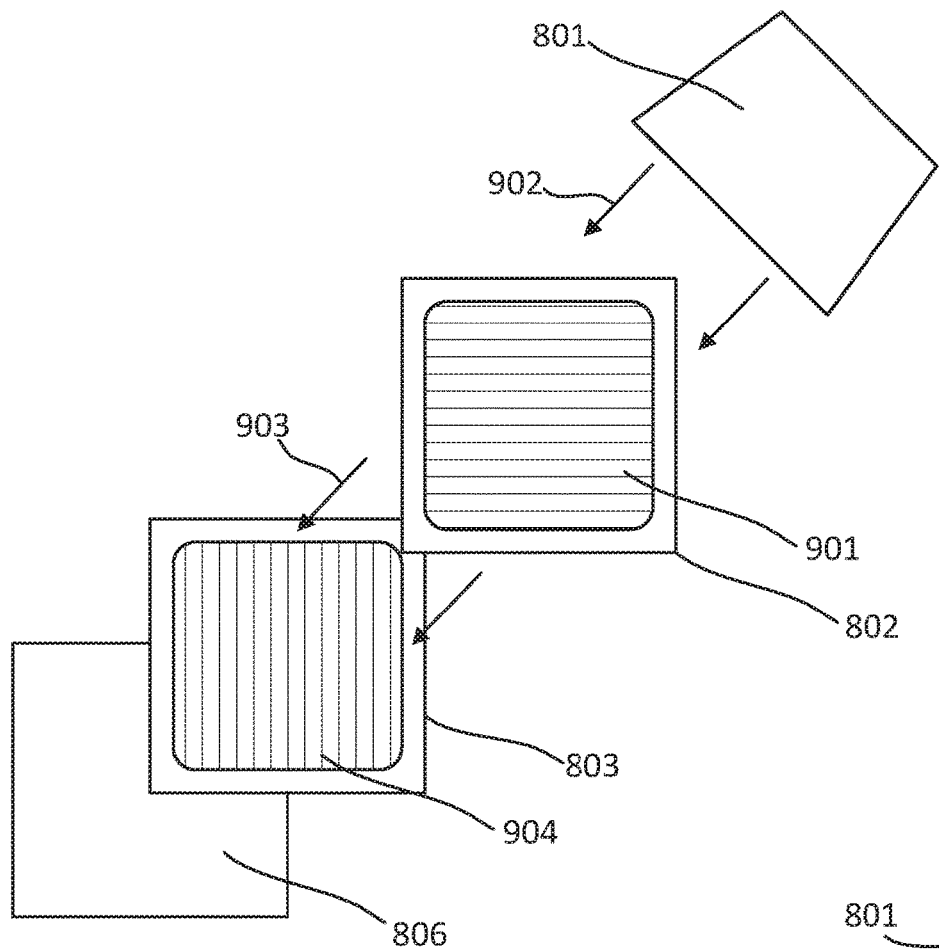
FIG. 9A illustrates an expanded view of a schematic of a device for measuring the collagen properties of a tissue sample having a light source, a detector plate, and two polarized plates.
Figure 9B:
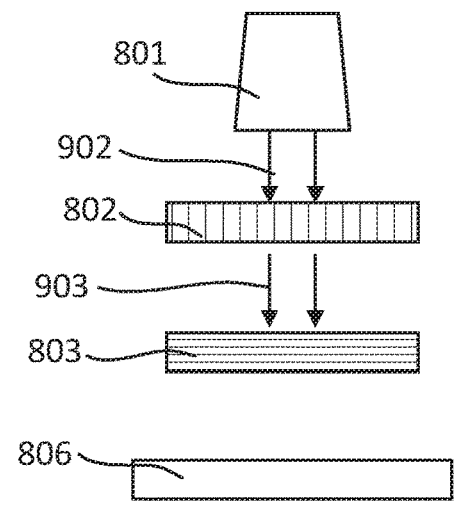
FIG. 9B illustrates a side view schematic of the device illustrated in FIG. 9A.

FIGS. 9A and 9B illustrate expanded perspective view and side view schematic, respectively, of the system 800. FIG. 9A illustrates a schematic of the orientation of the polarizing filter of each of the first polarizer 802 and the second polarizer 803. The first polarizer polarizes the light in a first orientation, which, in the illustrated example, is represented by lines 901 in a horizontal direction in the first polarizer. The second polarizer has a filter oriented so that it filters light in a direction offset by 90 degrees from the first polarizer. The light originates from the light source and travels to the first polarizer as indicated by arrows 902. The light is filtered in one direction by the first polarizer, and propagates to the second polarizer as indicated by arrows 903. The light is then filtered in an orthogonal direction by the second polarizer 803. The orthogonal configuration of the second polarizer is represented by the lines 904 in a vertical direction. As illustrated in FIG. 9B, the light is extinguished by the combination of being filtered in a first direction by the first polarizer and being filtered in a second direction by the second polarizer, where the second direction is orthogonal to the first direction. The absence of arrows between the second polarizer 803 and the detector plate 806 in FIG. 9B represents the absence of light waves passing therethrough to the detector plate. The first polarizer and second polarizer are positioned such that the light first passes through the first polarizer, with the second polarizer positioned farther from the light source than the first polarizer. The light entering the first polarizer can be a beam of light of undefined or mixed polarization. The first polarizer 802 polarizes the light as it passes through. The polarization of light waves that passes through can be oriented in a first direction. The second polarizer can be set up in a first position so that the plane in which it allows light to pass through is orthogonal to the plane in which the first polarizer allows light to pass through, such that the second polarizer's axis is oriented 90 degrees relative to the first polarizer axis. This arrangement of the polarizers relative to each other extinguishes (e.g., blocks) the light from passing through the second polarizer plate, so that no light is transmitted through the second polarizer. That means that with the polarizers arranged orthogonally to each other, substantially no light passes through to the detector plate. Any light that does pass through is leakage and considered to be an artifact.

Figure 10A:
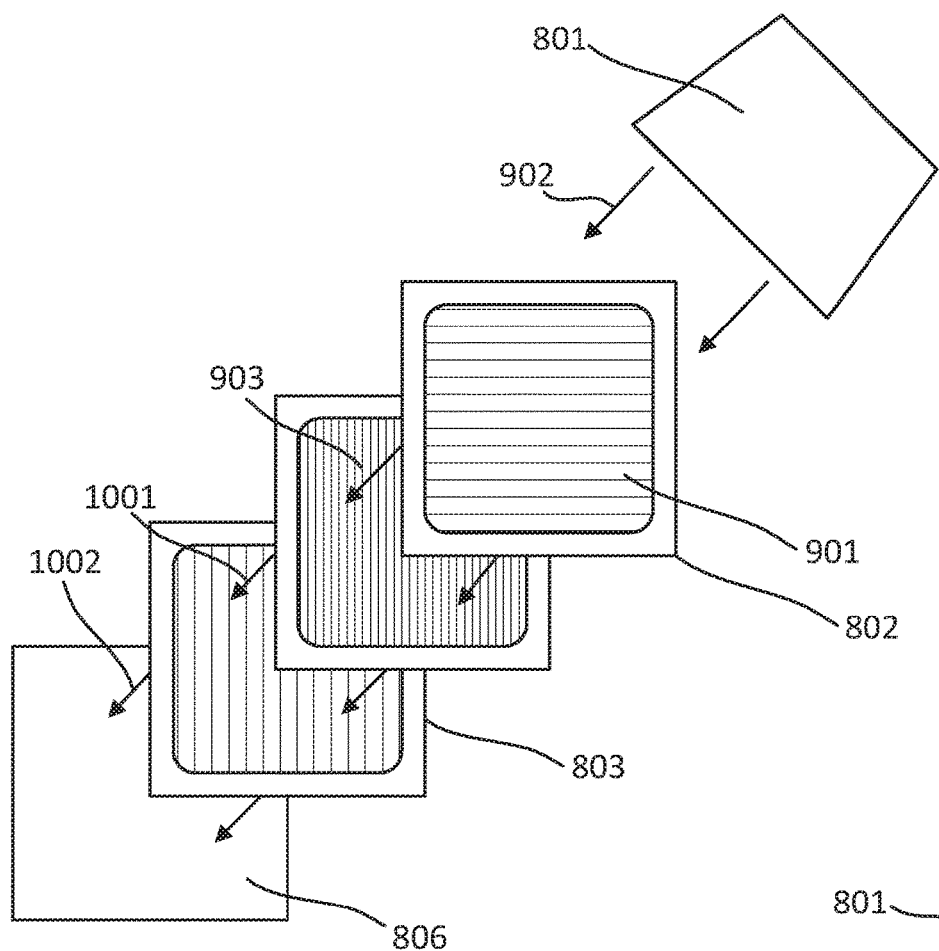
FIG. 10A illustrates an expanded view of a schematic of the device in FIG. 9A having a tissue sample positioned between the polarized plates.
Figure 10B:
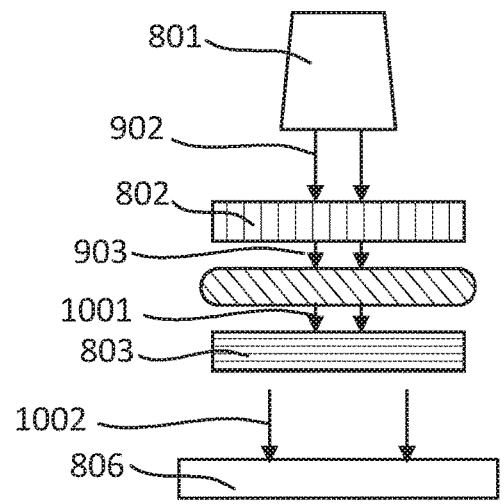
FIG. 10B illustrates a side view schematic of the device illustrated in FIG. 10A.

FIGS. 10A and 10B illustrate expanded perspective view and side view schematics, respectively, of the system 800 with a tissue sample 805 positioned between the first polarizer 802 and second polarizer 803. The transmission of polarized light passing through the tissue sample, represented by arrows 1001, is altered based on the birefringent properties of the collagen. The collagen bundles in the tissue sample rotate the polarization of the incident light. The light remains polarized as it passes through the tissue sample; the birefringence induces a rotation or phase shift between orthogonal polarization states. The light referred to as "rotated light" herein is rotated polarized light. After passing through the tissue, the light the tissue can be linearly polarized, elliptically polarized, circularly polarized, or any combination of linearly, elliptically, and circularly polarized, which changes the pattern of light that passes through and/or is extinguished by the second polarizer compared with the system in the absence of the tissue sample, for example, as illustrated in FIGS. 9A and 9B. The amount of rotation and the relative spatial location indicates the orientation and density of collagen bundles and/or fibers in the tissue sample. The optical property of birefringence in collagen bundles causes the polarization angle of light transmitted therethrough to rotate so that at least a portion thereof is no longer blocked by the second polarizer. The intensity of the rotated light passes through the second polarizer in proportion to density of aligned collagen bundles, and is not extinguished by the second polarizer. The light that has not rotated by the tissue sample is substantially extinguished by the second polarizer. The rotated light, as it passes through the second polarizer, represented by arrows 1002, appears as a pattern, for example, bright bands, on an otherwise unilluminated detector plate. The illuminated regions are a visual indicator of where the collagen bundles are located, as well as their orientations, densities of the collagen fibers in the collagen bundles, and/or the densities of the collagen bundles in the tissue sample. As such, the spatial locations or patterns of the transmitted light as well as their intensities can be used to determine collagen orientation, the densities of the collagen fibers in the collagen bundles, and/or the densities of the collagen bundles because the density of the collagen bundles within the tissue sample affects the degree of rotation of the polarization as the light it passes through the sample. The density of the collagen fibers within a bundle can also affect the degree of rotation of the polarized light passing through the bundle. The more dense the collagen bundles are in the sample and/or the more dense the collagen fibers are in the bundles, the more the light will rotate as it passes through the tissue sample and the brighter the resulting light will be on the detector plate. Thus, the density of the collagen fibers in the collagen bundles and/or the density of the collagen bundles in the tissue can be determined by the brightness or intensity of the light on the detector plate.

Figure 11A:
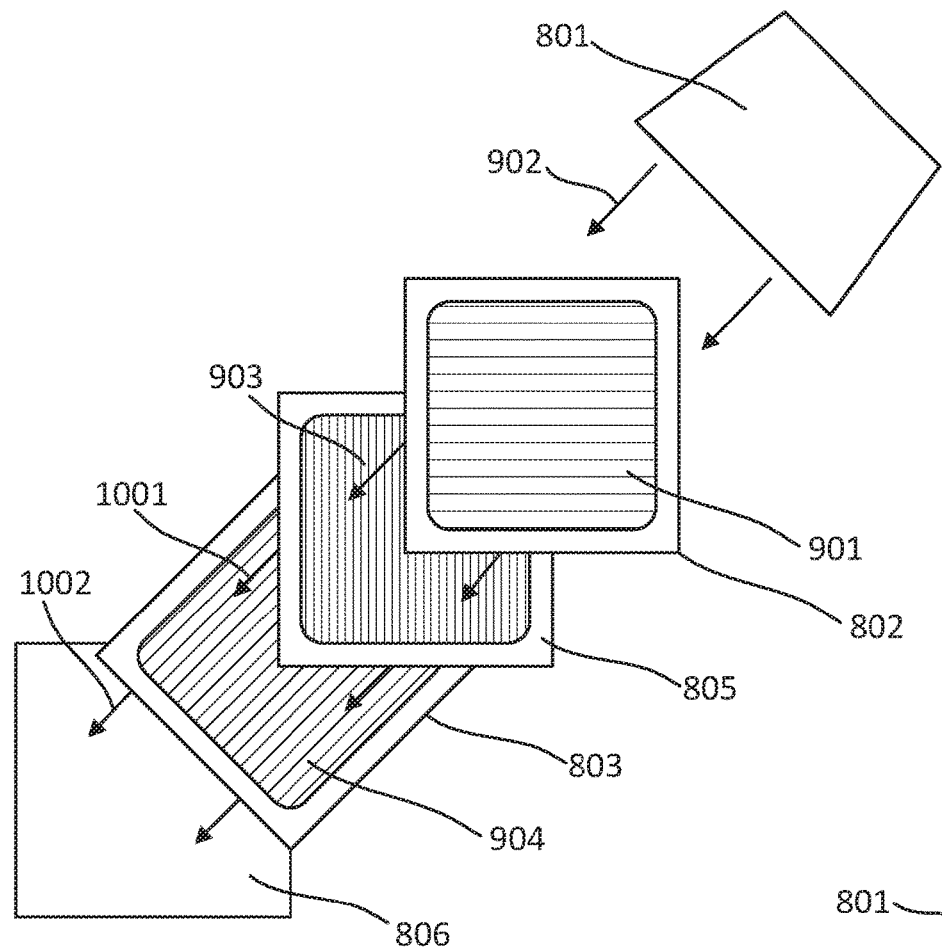
FIG. 11A illustrates an expanded view of the device illustrated in FIG. 10A, where one of the polarized plates is rotated 45 degrees.
Figure 11B:
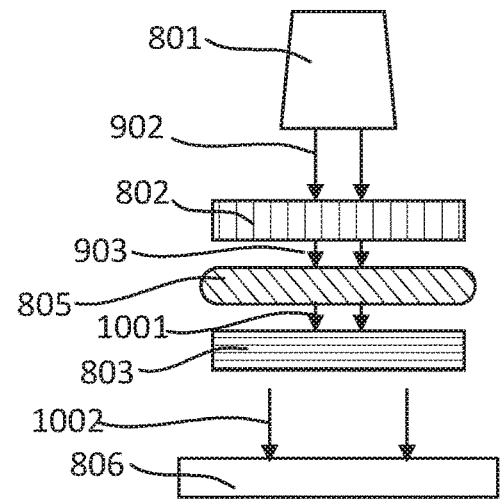
FIG. 11B illustrates a side view of the device illustrated in FIG. 11A.

FIGS. 11A and 11B illustrate expanded perspective view and side view schematics, respectively, of the system 800 with a tissue sample 805 positioned between the first polarizer 802 and second polarizer 803. Arrows 902 represent the unpolarized light from the light source. In this example, lines 904 in the second polarizer 803 of FIG. 11A represent that the second polarizer is rotated at an angle different from 90 degrees relative to the first polarizer, in the present example, about 45 degrees. Arrows 1001 represent the light that passes through the tissue sample. Arrows 1002 in FIGS. 11A and 11B illustrate light that is transmitted past the second polarizer 803 and illuminates the detector plate 806. Because the collagen bundles in the tissue rotate the polarization of the light from the first polarizer, depending on the density and/or alignment of the bundles, rotating the second polarizer can bring it into and out of alignment with the polarization of the rotated light, thereby permitting a user to improve the visualization on the detector plate of one or more particular sets or regions of the tissue with similar polarization properties, as well as to distinguish between different sets of regions. For example, regions in which the orientations of the collagen bundles are more aligned can provide higher intensities on the detector plate compared with regions with random orientations. Similarly, intensities can increase with increasing density. Rotating the polarizer can also provide information on the depth of the collagen bundles and/or fibers as well as changes in collagen bundle orientation throughout the tissue sample. This is particularly helpful because the collagen bundles are not all oriented in the same way, throughout the entire thickness of the tissue of a pericardial sac. Because the method relates to the relative rotations of the first and second polarizers, either or both may be rotated.

Figure 12A:
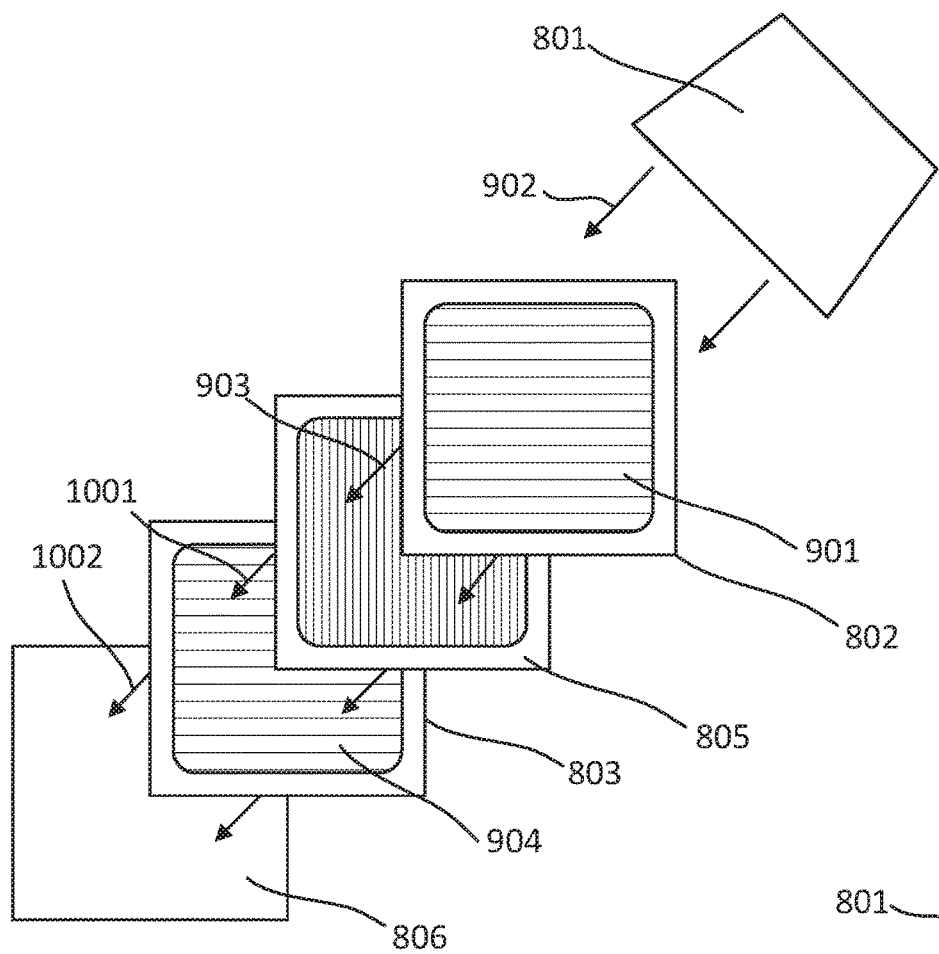
FIG. 12A illustrates an expanded view of the device illustrated in FIG. 10A, where one of the polarized plates is rotated 90 degrees.
Figure 12B:
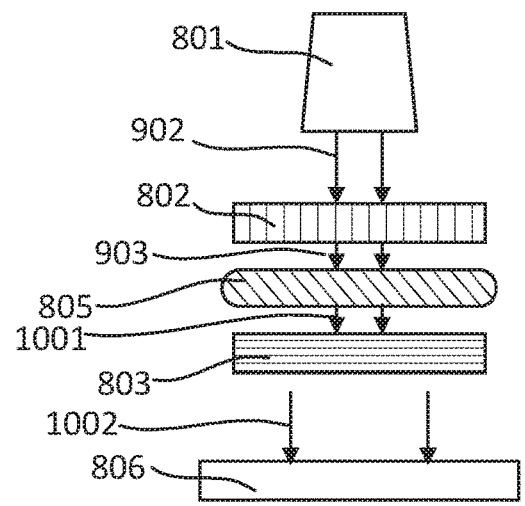
FIG. 12B illustrates a side view of the device illustrated in FIG. 12A.

FIGS. 12A and 12B illustrate expanded perspective view and side view schematics, respectively, of the system 800 with a tissue sample 805 positioned between the first polarizer 802 and second polarizer 803. The light that passes through the first polarizer, represented by arrows 903, is polarized in a linear orientation. Portions of the light are rotated by collagen bundles in the tissue sample, as discussed above. The rotated light is represented by arrows 1001. The lines 904 in the second polarizer 803 of FIG. 12A represent that the second polarizer is oriented so that light passing through it is polarized in the same orientation as the light that passes through the first polarizer. Arrows 1002 indicate light that is transmitted to the detector plate 806 after passing through the second polarizer. In this particular configuration of first polarizer, tissue sample, and second polarizer, the rotated light appears as darker patterns on the detector plate, for example, darker bands. This occurs when rotated light passing through the second polarizer has a polarization angle perpendicular to the polarization angle of the second polarizer. The second polarizer blocks the rotated light from passing through and appears as dark patterns on the detector plate. The second polarizer plate is not limited to the orientations illustrated in FIGS. 9A-12B, but can be rotated to any angle from zero to 360 degrees, which can provide information on the collagen bundle orientation. By varying the rotation of the second plate, the orientation of the collagen bundles disposed at any angle within the tissue sample can be determined. A user can rotate the second polarizer to find all the collagen bundles, so that they each can be spatially oriented or mapped. A user can rotate the second polarizer to find the collagen bundles at a first depth of the tissue's overall thickness. A user can rotate the second polarizer to find the collagen bundles at varying depths of the tissue. During the rotation of the second polarizer, when a bright feature appears on the detector plate, its brightness can be measured to determine the density of the corresponding collagen bundle in the sample and/or the density of the collagen fibers in the collagen bundles. In other exemplary embodiments, the first polarizer can be rotated, or both the first and second polarizers can be rotated.

Figure 13A:
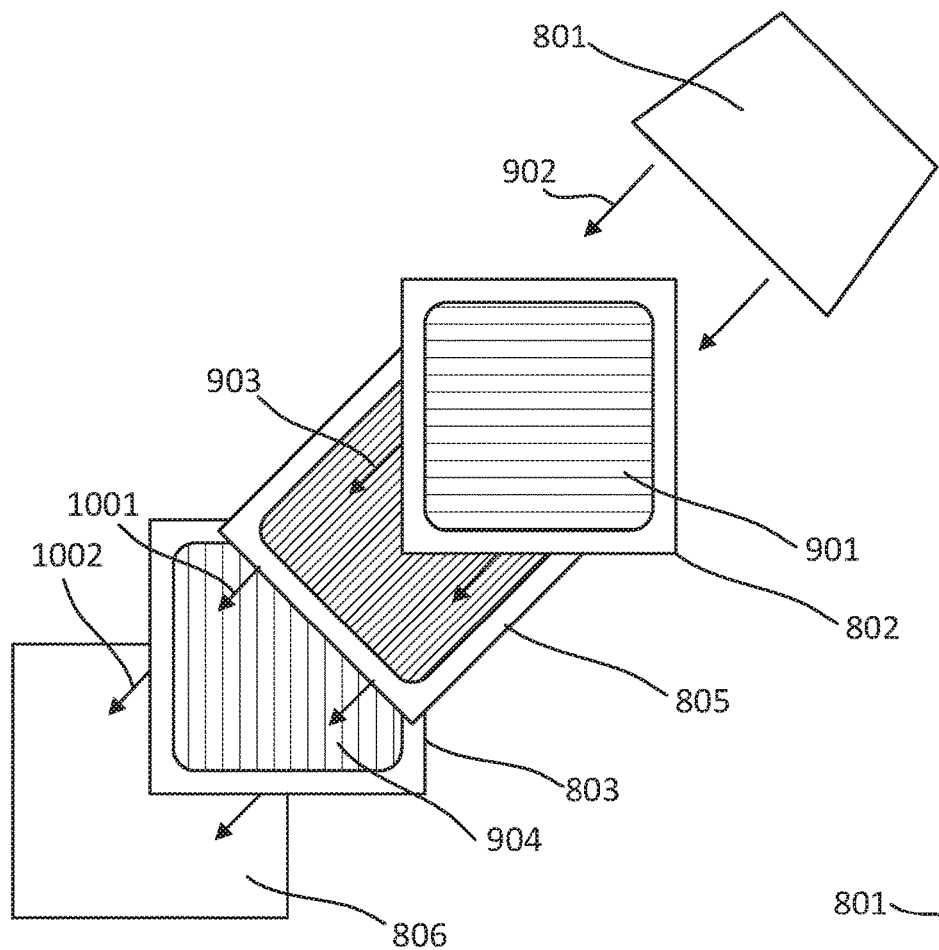
FIG. 13A illustrates an expanded view of the device illustrated in FIG. 10A, where the tissue sample is rotated 45 degrees.
Figure 13B:
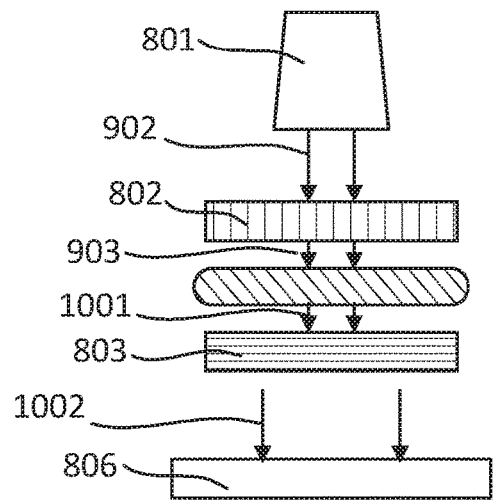
FIG. 13B illustrates a side view of the device illustrated in FIG. 13A.

FIGS. 13A and 13B illustrate expanded perspective view and side view schematics, respectively, of the system 800 with a tissue sample 805 positioned between the first polarizer 802 and second polarizer 803. Rotating the tissue can make it easier to find the collagen bundles. The light that passes through the first polarizer, represented by arrows 903, is polarized in a linear orientation. The light is rotated as it passes through the tissue sample, and this rotated light is represented by arrows 1001. In FIG. 13A, the first polarizer and second polarizer are in a configuration where the light in the second polarizer is polarized in an orthogonal direction to light filtered by the first polarizer. This is represented by lines 904 in the second polarizer 803. In FIG. 13A, the tissue sample has been rotated 45 degrees, as compared to its position in FIG. 10A. The tissue sample can be rotated any amount from zero to 360 degrees. Rotating the tissue sample is another method of adjusting the light that is transmitted through the system 800 onto the detector plate 806 so that the orientation, density of the collagen bundles in the sample and/or and density of all the collagen fibers in the collagen bundles can be determined, just as with rotating the second polarizer. Arrows 1002 in FIGS. 13A and 13B illustrate light that is transmitted past the second polarizer 803 and illuminates the detector plate 806.

The process for determining the collagen bundle orientation and density of the tissue, as well as any other measurements, can be applied to an entire bovine pericardial sac, which is the entire outer pericardia, or portions thereof, such as windows cut from the pericardial tissue and/or leaflet sized patches. The leaflet sized patches are pieces of the pericardia that have been cut to a size that is usable to make the leaflets of a heart valve.

Determining the collagen bundle orientation, the density of the collagen bundles in the tissue, and/or the density of the collagen fibers in the collagen bundles according to the methods described herein can be used to determine how a bovine pericardia tissue sample should be cut to make leaflets for a heart valve implant. Each layer of tissue in the pericardial sac can have its collagen bundles oriented differently form the other layers. The dominant orientation is the layer that has the greatest density of collagen bundles. The collagen bundle orientation and density vary over the various anatomical regions of the pericardial sac. The method described herein can be used to map the dominant collagen bundle orientations over the entire sac. The information on collagen bundle orientation provided by this mapping of the pericardial sac tissue can be used to optimize the location of where a leaflet can be cut from the pericardial sac tissue.

The collagen bundle orientation varies between the tissue layers in the pericardial sac. The rotation of one of the polarizers and/or the tissue sample in the method described herein can be used to determine the dominant orientation location. By using the optical method described herein, the orientation of the collagen bundles can be determined.

The collagen bundle orientation can be determined at any point during the process of making a leaflet. Upon determining how the collagen bundles are oriented, the tissue sample can be milled into an appropriate thickness and cut into leaflet shapes as described herein. The milling of the tissue to a particular thickness can be done by known methods in the art such as skiving, laser-cutting, or laser ablation of the tissue to the desired thickness, profile, and/or shape. In one exemplary embodiment, the collagen bundle orientation and/or density is not determined until after the tissue is milled to the appropriate thickness.

Figure 14:
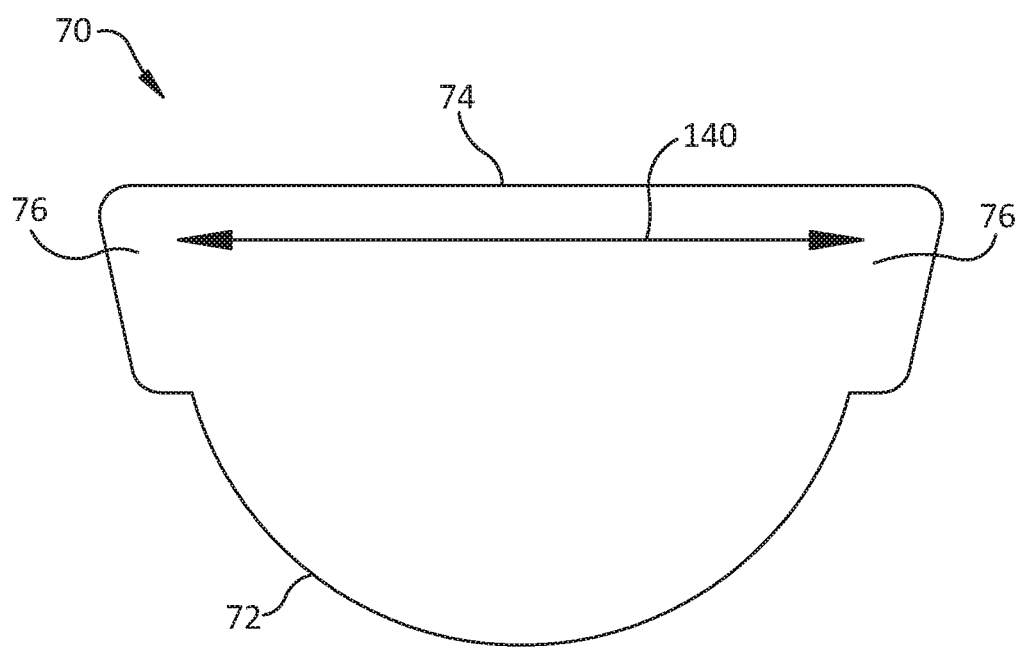
FIG. 14 illustrates a schematic of a leaflet of a valve with a collagen bundle orientation according to an exemplary embodiment.

In one type of valve implant for example, as illustrated in FIG. 14, each leaflet 70 can be cut to have an upper free edge 74, a lower edge 72, and two commissure flaps 76 extending between the lower edge 72 and the upper free edge 74. The upper free edge 74 can be cut along a line parallel to the direction the majority of the collagen bundles extend, indicated by line 140.

The methods and devices described herein are not limited in use to determining the collagen bundle and/or fiber orientation and density of bovine pericardial tissue. They can be used with any tissue sample that can be used in the making of a prosthetic valve, other prosthetic, or for any other purpose.

Furthermore, the methods, devices, and systems are useful in any situation in which a piece of collagenous tissue is desired with greater strength in one dimension than the other, for example, in patches that experience more stress on one direction, as well as in devices incorporating such tissue. These disclosure are also useful where selecting tissue with greater isotropy is desirable.

Further, although some of the embodiments have been described herein in the context of a particular implementation in a particular environment for a particular purpose, those of ordinary skill in the art should recognize that its usefulness is not limited thereto and that the various embodiments can be beneficially implemented in any number of environments for any number of purposes. Accordingly, the claims set forth below should be construed in view of the full breadth and spirit of the embodiments as disclosed herein. While the foregoing description includes many details and specificities, it is to be understood that these have been included for purposes of explanation only, and are not to be interpreted as limitations of the various embodiments. Modifications to the embodiments described above can be made without departing from the spirit and scope of this description.

What is claimed is:

1. A method for manufacturing a bioprosthetic tissue leaflet from a collagenous tissue, the method comprising:
   illuminating a piece of tissue comprising collagen with a light source having a linear polarization;
   passing light transmitted through the piece of tissue through a linear polarizer;
   detecting a first pattern in the light passed through the linear polarizer;
   determining a first orientation or a first density of collagen bundles in at least a portion of the piece of tissue from the first detected pattern;
   after determining the first orientation or first density of the collagen bundles, rotating the linear polarizer and detecting a second pattern of light passed through the linear polarizer;
   determining a second orientation or a second density of collagen bundles in at least a portion of the piece of tissue from the second detected pattern;
   selecting an area on the piece of tissue for a bioprosthetic tissue leaflet based on the first and second orientations or densities of collagen bundles; and
   cutting the bioprosthetic tissue leaflet including the selected area.

2. The method of claim 1, wherein illuminating the piece of tissue comprises illuminating a piece of pericardium, dura mater, peritoneum, diaphragm, or intestinal submucosa.

3. The method of claim 1, wherein illuminating the piece of tissue comprises illuminating a piece of pericardium.

4. The method of claim 3, wherein illuminating the piece of pericardium comprises illuminating a piece of bovine or porcine pericardium.

5. The method of claim 1, wherein illuminating the piece of tissue comprises illuminating a piece of wet tissue or a piece of dry tissue.

6. The method of claim 1, wherein illuminating the piece of tissue comprises illuminating a piece of fixed tissue or a piece of unfixed tissue.

7. The method of claim 1, wherein illuminating the piece of tissue comprises changing an angle of incidence between the light source and the piece of tissue.

8. The method of claim 1, wherein illuminating the piece of tissue comprises illuminating the piece of tissue with a specific wavelength of light.

9. The method of claim 1, wherein passing light transmitted through the piece of tissue through the linear polarizer comprises passing light transmitted through the piece of tissue through a linear polarizer parallel with the linear polarization of the light source.

10. The method of claim 1, wherein passing light transmitted through the piece of tissue through the linear polarizer comprises passing light transmitted through the piece of tissue through a linear polarizer perpendicular to the linear polarization of the light source.

11. The method of claim 1, wherein passing light transmitted through the piece of tissue through the linear polarizer comprises passing light transmitted through the piece of tissue through a linear polarizer that is not parallel with nor perpendicular to the linear polarization of the light source.

12. The method of claim 1, wherein detecting the first or second pattern comprises projecting the first or second pattern on a detector plate; displaying the first or second pattern on a monitor; or imaging the first or second pattern with a camera.

13. The method of claim 1, wherein detecting the first or second pattern comprises storing a light pattern on a computer.

14. The method of claim 1, wherein detecting the first or second pattern comprises detecting a light pattern including at least one elongate feature, line, streak, or band.

15. The method of claim 1, wherein determining the first or second orientation or the first or second density comprises determining an intensity of at least a portion of the first or second pattern; determining a direction of at least a portion of the first or second pattern; or determining the first or second orientation of at least a portion of the first or second pattern, respectively.

16. The method of claim 1, wherein selecting the area comprises selecting an area in which the collagen bundle first or second orientations are randomly distributed.

17. The method of claim 1, wherein selecting the area comprises selecting an area in which the collagen bundle first or second orientations are aligned.

18. The method of claim 17, wherein selecting the area includes laying-out a free-edge of the bioprosthetic tissue leaflet parallel with the alignment of the collagen bundles.

19. The method of claim 1, wherein cutting the bioprosthetic tissue leaflet includes die cutting a bioprosthetic tissue leaflet or laser cutting a bioprosthetic tissue leaflet.

20. The method of claim 1, further comprising rotating the light source.

* * * * *